United States Patent [19]
Mori et al.

[11] Patent Number: 5,600,034
[45] Date of Patent: Feb. 4, 1997

[54] METHOD FOR PRODUCING ALLYL ALCOHOLS

[75] Inventors: Tomoyuki Mori; Hiroshi Kameo; Shinji Isogai; Soichiro Saita, all of Kurashiki, Japan

[73] Assignee: Mitsubishi Chemical Corporation, Tokyo, Japan

[21] Appl. No.: 560,637

[22] Filed: Nov. 20, 1995

[30] Foreign Application Priority Data

Nov. 28, 1994 [JP] Japan .................................. 6-317517

[51] Int. Cl.$^6$ ............................. C07C 29/00; C07C 33/02
[52] U.S. Cl. ...................... 568/908; 568/687; 568/909.5
[58] Field of Search .............................. 568/908, 909.5

[56] References Cited

U.S. PATENT DOCUMENTS

| | | | |
|---|---|---|---|
| 3,518,315 | 6/1970 | Smutny | 568/908 |
| 4,990,698 | 2/1991 | Wada et al. | 568/909.5 |
| 5,057,631 | 10/1991 | Tokitoh et al. | 568/909.5 |
| 5,169,981 | 12/1992 | Packett | 568/909.5 |
| 5,345,007 | 9/1994 | Monflier et al. | 568/909.5 |

FOREIGN PATENT DOCUMENTS 2885536 3/1990 Japan .

Primary Examiner—Joseph E. Evans
Attorney, Agent, or Firm—Oblon, Spivak, McClelland, Maier & Neustadt, P.C.

[57] ABSTRACT

A method for producing allyl alcohols, which comprises heat-treating diallyl ethers in the presence of a catalyst containing a palladium compound and a phosphorus compound to convert them to allyl alcohols, wherein the heat treatment is conducted under such conversion reaction conditions that the value of function F represented by the following formula is within a range of $0 \leq F < 100$, the concentration of allyl alcohols in the conversion reaction solution is not higher than 20 wt %, and the Pd concentration in the conversion reaction solution is within a range of from 0.005 to 1.0 wt %:

$$F = \theta t \cdot [Pd] \cdot (t - 100)$$

wherein $\theta t$ is the conversion reaction time (hours), $[Pd]$ is the Pd concentration (wt %) in the conversion reaction solution, and T is the conversion reaction temperature (°C.)

19 Claims, 1 Drawing Sheet

METHOD FOR PRODUCING ALLYL ALCOHOLS

BACKGROUND OF THE INVENTION

1. Field of the Invention

The present invention relates to a method for producing allyl alcohols. Particularly, it relates to a method for producing allyl alcohols, wherein diallyl ethers are heat-treated in the presence of a catalyst containing a palladium compound and a phosphorus compound to convert them to allyl alcohols.

2. Discussion of Background

Alkadienols, especially octadienols including octa-2,7-dien-1-ol, are industrially important compounds, as intermediates for producing n-octanol or its esters.

Heretofore, as a method for producing alkadienols, a method is known in which a conjugated alkadiene and water are subjected to a dimerization reaction in the presence of a catalyst containing a palladium compound and a phosphorus compound and, if necessary, carbon dioxide. For example, Japanese Examined Patent Publication No. 10565/1975 discloses a dimerization reaction employing triphenylphosphine as a ligand of the palladium compound. However, the yield and selectivity for alkadienols are inadequate, and high boiling point substances such as diallyl ethers (e.g. dialkadienyl ethers) are produced as by-products.

Production of such high boiling point substances as by-products consumes the starting material conjugated alkadiene uselessly, whereby the yield of desired allyl alcohols (e.g. alkadienols) will be reduced. Besides, when the catalyst solution is recycled for use, the high boiling by-products tend to accumulate in the recycled catalyst solution and show a chemical inhibitory action against the catalytic activities, or they tend to increase the viscosity of the recycled catalyst solution to substantially hinder the reaction.

Further, Japanese Unexamined Patent Publication No. 88536/1990 discloses a method in which alkadienols are formed from a conjugated alkadiene and water, then from the obtained reaction solution, alkadienols and the solvent are separated to obtain a solution containing dialkadienyl ethers and a palladium compound, and the solution is heat-treated at a temperature of at least 90° C. to decompose dialkadienyl ethers to alkatrienes, etc. However, the method disclosed in this Japanese Unexamined Patent Publication No. 88536/1990 is not a method for recovering useful components by the decomposition of dialkadienyl ethers, as the decomposition products are water and alkatrienes, etc., although it is effective to decompose and remove dialkadienyl ethers as high boiling point by-products. Besides, in the method disclosed in Japanese Unexamined Patent Publication No. 88536/1990, desired alkadienols are also likely to be decomposed to alkatrienes, etc. Accordingly, it has a drawback that alkadienols have to be separated by distillation under an industrially extremely difficult condition such as 1.8 mmHg prior to the heat treatment. Further, in such a case, due to the distillation under a high vacuum condition and the accompanying heat treatment, decomposition products of the treated solution will be distilled. Consequently, the palladium and the phosphorus compound are concentrated and precipitated, whereby an industrial operation will be extremely difficult.

Under these circumstances, it has been desired to develop a method for producing allyl alcohols (such as alkadienols), whereby diallyl ethers (such as dialkadienyl ethers) can be effectively used.

SUMMARY OF THE INVENTION

The present invention has been made under the above circumstances, and it is an object of the present invention to provide a method for producing allyl alcohols, wherein diallyl ethers are used as the starting material, particularly an industrially advantageous method for producing allyl alcohols, which can be applied also to a hydration dimerization reaction solution containing diallyl ethers as by-products.

Accordingly, in a first aspect, the present invention provides a method for producing allyl alcohols, which comprises heat-treating diallyl ethers in the presence of a catalyst containing a palladium compound and a phosphorus compound to convert them to allyl alcohols, wherein the heat treatment is conducted under such conversion reaction conditions that the value of function F represented by the following formula is within a range of $0 \leq F < 100$, the concentration of allyl alcohols in the conversion reaction solution is not higher than 20 wt %, and the Pd concentration in the conversion reaction solution is within a range of from 0.005 to 1.0 wt %:

$$F = \theta t \cdot [Pd] \cdot (T - 100)$$

wherein $\theta t$ is the conversion reaction time (hours), [Pd] is the Pd concentration (wt %) in the conversion reaction solution, and T is the conversion reaction temperature (°C.).

In a second aspect, the present invention provides a method for producing allyl alcohols, which comprises subjecting a conjugated alkadiene and water to a hydration dimerization reaction in the presence of a catalyst containing a palladium compound and a phosphorus compound and, if necessary, carbon dioxide to obtain a hydration dimerization reaction solution containing allyl alcohols and diallyl ethers as by-products, and then heat-treating the diallyl ethers in the reaction solution for conversion to allyl alcohols, wherein the heat treatment is conducted under such conversion reaction conditions that the value of function F represented by the following formula is within a range of $0 \leq F < 100$, the concentration of the allyl alcohols in the conversion reaction solution is not higher than 20 wt %, and the Pd concentration in the conversion reaction solution is within a range of from 0.005 to 1.0 wt %:

$$F = \theta t \cdot [Pd] \cdot (T - 100)$$

wherein $\theta t$ is the conversion reaction time (hours), [Pd] is the Pd concentration (wt %) in the conversion reaction solution, and T is the conversion reaction temperature (°C.).

In a third aspect, the present invention provides a method for producing allyl alcohols, which comprises subjecting a conjugated alkadiene and water to hydration dimerization reaction in a solvent in the presence of a catalyst containing a palladium compound and a phosphorus compound and, if necessary, carbon dioxide to obtain a hydration dimerization reaction solution containing allyl alcohols and diallyl ethers as by-products, and then heat-treating the diallyl ethers in the reaction solution for conversion to allyl alcohols, wherein the heat treatment is conducted when the allyl alcohols are separated by distillation from the reaction solution under such conversion reaction conditions that the value of function F represented by the following formula is within a range of $0 \leq F < 100$, the concentration of allyl alcohols in the conversion reaction solution is not higher than 20 wt %, and the Pd concentration in the conversion reaction solution is within a range of from 0.005 to 1.0 wt %:

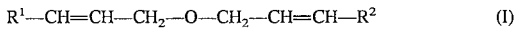

$$F = \theta t \cdot [Pd] \cdot (T - 100)$$

wherein θt is the conversion reaction time (hours), [Pd] is the Pd concentration (wt %) in the conversion reaction solution, and T is the conversion reaction temperature (°C.).

DETAILED DESCRIPTION OF THE PREFERRED EMBODIMENTS

Figure 1:
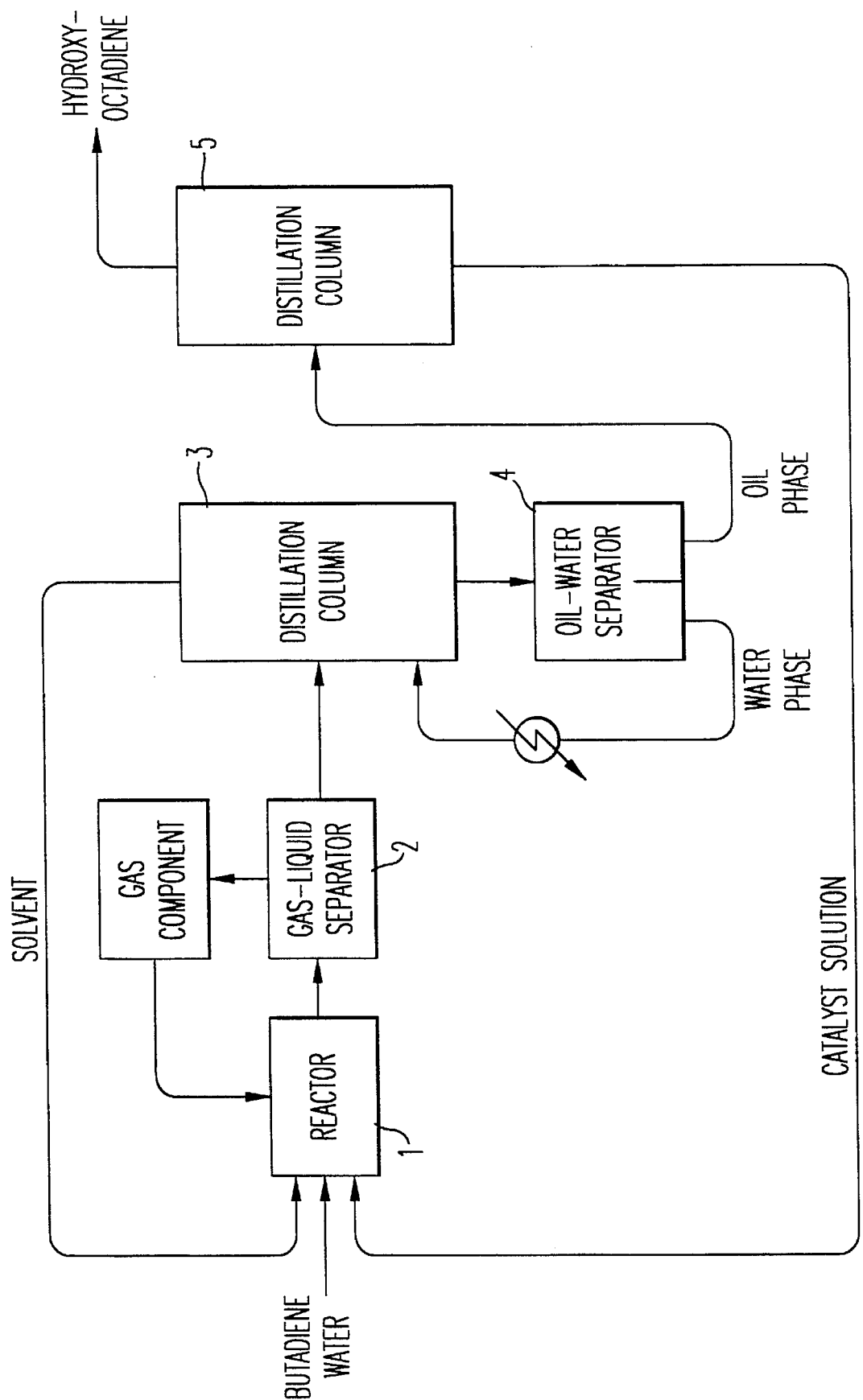
FIG. 1 is a flowchart of the process used in Example 8.

Now, the present invention will be described in detail. Firstly, the first aspect of the present invention will be described.

The starting material diallyl ethers are represented by the following formula (I):

$$R^1-CH=CH-CH_2-O-CH_2-CH=CH-R^2 \quad (I)$$

wherein each of $R^1$ and $R^2$ is a hydrogen atom, a saturated hydrocarbon group or an unsaturated hydrocarbon group, and $R^1$ and $R^2$ may be the same or different.

When $R^1$ or $R^2$ in the formula (I) is a hydrocarbon group, its carbon number is usually from 1 to 12, preferably from 1 to 10. The compounds of the formula (I) may, for example, be dialkenyl ethers such as dipropenyl ether, dibutenyl ether, dipentenyl ether, dihexenyl ether, diheptenyl ether, dioctenyl ether, dinonenyl ether, didecenyl ether, propenyl butenyl ether, propenyl hexenyl ether, propenyl octenyl ether, propenyl decenyl ether, butenyl pentenyl ether and butenyl hexenyl ether; dialkadienyl ethers such as dipentadienyl ether, dihexadienyl ether, diheptadienyl ether, dioctadienyl ether, dinonadienyl ether, didecadienyl ether, pentadienylhexadienyl ether, pentadienylheptadienyl ether, pentadienyloctadienyl ether, pentadienylnonadienyl ether and pentadienyldecadienyl ether; or alkenylalkadienyl ethers such as propenylpentadienyl ether, butynylpentadienyl ether, pentenylpentadienyl ether, hexenylpentadienyl ether, heptenylpentadienyl ether, propenyloctadienyl ether, butenyloctadienyl ether, pentenyloctadienyl ether, hexenyloctadienyl ether, heptenyloctadienyl ether and octenyloctadienyl ether.

The above diallyl ethers will give allyl alcohols by heat treatment in the presence of a catalyst containing a palladium compound and a phosphorus compound. Namely, diallyl ethers will be converted to allyl alcohols and unsaturated hydrocarbons such as alkadienes and alkatrienes.

The allyl alcohols as desired products of the present invention are represented by the following formula (II):

$$R^3-CH=CH-CH_2OH \quad (II)$$

wherein $R^3$ is a hydrogen atom, a saturated hydrocarbon group or an unsaturated hydrocarbon group.

In the present invention, it is advantageous to use dialkadienyl ethers as the starting material diallyl ethers, because alkadienols obtainable from the dialkadienyl ethers are industrially important as intermediates for various products. As the dialkadienyl ethers, it is particularly advantageous to use dioctadienyl ether.

The form and the valency of the palladium compound to be used as the catalyst in the present invention is not particularly limited. The palladium compound may, for example, be a metal palladium such as palladium black or palladium metal supported on a carrier; a zerovalent palladium complex such as bis(t-butylisonitrile)palladium (0), bis(t-amylisonitrile)palladium (0), bis(cyclohexylisonitrile)palladium (0), bis(phenylisonitrile)palladium (0), bis(p-toluylisonitrile)palladium (0), bis(2,6-dimethylphenylisonitrile)palladium (0), tris(dibenzylideneacetone)dipalladium (0), (1,5-cyclooctadiene) (maleic anhydride)palladium (0), bis(norbornene)(maleic anhydride)palladium (0), bis(maleic anhydride)(norbornene)palladium (0), (dibenzylideneacetone)(bipyridyl)palladium (0), or (p-benzoquinone) (o-phenanthroline)palladium (0); a tetrakis(phosphine)palladium, tris(phosphine)palladium or bis(phosphine)palladium complex having a phosphine compound as a ligand, such as tetrakis(triphenylphosphine)palladium (0), tris-(triphenylphosphine)palladium (0), bis(tritolylphosphine)palladium (0), bis(trixylyl)palladium (0), bis(trimethylphosphine)palladium (0), bis(tritetramethylphenyl)palladium (0) or bis(trimethylmethoxyphenylphosphine)palladium (0), or the corresponding tetrakis(phosphite)palladium, tris(phosphite)palladium or bis(phosphite)palladium complex having a phosphite compound as a ligand; an inorganic acid salt of palladium such as palladium (II) chloride, palladium (II) nitrate, tetraaminedichloropalladium (II) or disodiumtetrachloropalladium (II); a palladium carboxylate such as palladium (II) acetate, palladium (II) benzoate or palladium (II) αpicolate; a chelate compound of palladium such as bis(acetylacetone)palladium (II) or bis(8-oxyquinoline)palladium (II); or a bivalent palladium complex such as bis(allyl)palladium (II), (η-allyl) (η-cyclopentadienyl)palladium (II), (η-cyclopentadienyl) (1,5-cyclooctadiene)palladium (II) tetrafluoroborate, bis(benzonitrile)palladium (II) acetate, di-μ-chloro-dichlorobis(triphenylphosphine) dipalladium (II), bis(tri-n-butylphosphine) palladium (II) acetate or 2,2-bipyridylpalladium (II) acetate.

Among the above palladium compounds, tetrakis(triphenylphosphine)palladium (0), bis(tritolylphosphine)palladium (0), bis(trixylyl)palladium (0), bis(trimethylmethoxyphenylphosphine)palladium (0), palladium (II) acetate or bis(acetylacetone)palladium (II) is preferred.

As the phosphorus compound to be used as the catalyst in the present invention, various phosphines, phosphinites, phosphonites and phosphites may be mentioned. Specific examples thereof include a trialkylphosphine such as trioctylphosphine, tributylphosphine or dimethyloctylphosphine; a tricycloalkylphosphine such as tricyclohexylphosphine; a triarylphosphine such as triphenylphosphine, tritolylphosphine, trixylylphosphine, trimesitylphosphine, tris(tetramethylphenyl)phosphine, diphenyl-p-chlorophenylphosphine or tris(p-methoxyphenyl) phosphine; a tertiary alkylarylphosphine such as diphenylethylphosphine, dimethylphenylphosphine, bis(diphenylphosphine)methane or 1,2-bis(diphenylphosphine)ethane; an alkylphosphinite such as dioctyloctoxyphosphine or dibutylbutoxyphosphine; an arylphosphinite such as diphenylphenoxyphosphine, ditolyltolyloxyphosphine or dixylylxylyloxyphosphine; an alkylarylphosphinite such as diphenylethoxyphosphine or diethylphenoxyphosphine; an alkylphosphonite such as octyldioctoxyphosphine or butylbutoxyphosphine; an arylphosphonite such as phenyldiphenoxyphosphine, tolylditolyloxyphosphine or xylyldixylyloxyphosphine; an alkylarylphosphonite such as phenyldiethoxyphosphine or ethyldiphenoxyphosphine; a trialkylphosphite such as trioctylphosphite, tributylphosphite or dimethyloctylphosphite; a tricycloalkylphosphite such as tricyclohexylphosphite; a triarylphosphite such as triphenylphosphite, tritolylphosphite or trixylylphosphite; and an alkylarylphosphite such as diphenylethylphosphite or dimethylphenylphosphite.

Among the above phosphorus compounds, a hydrophobic phosphine such as triphenylphosphine, tritolylphosphine, trixylylphosphine, trimesitylphosphine or tris(tetramethylphenyl)phosphine is preferred.

Further, water-soluble phosphines of the following formula (III) can be used:

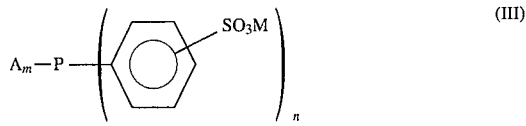

wherein A is a phenyl group, M is an alkali metal, m is an integer of from 0 to 2, and n is an integer of from 1 to 3, provided that m+n=3.

Still further, cyclic phosphites of the following formulas (IV) and (V) can also be used:

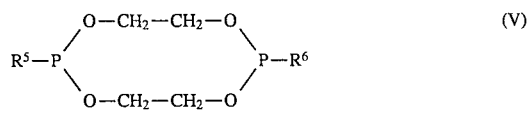

wherein each of $R^4$, $R^5$ and $R^6$ which are independent of one another, is an alkyl group such as methyl, ethyl or nonyl, an aryl group such as phenyl, tolyl or naphthyl, a hydroxyalkyl group such as hydroxymethyl, hydroxyethyl or hydroxypentyl, an alkoxyalkyl group such as ethoxymethyl, an aryloxyalkyl group such as phenoxymethyl, or an acyloxyalkyl group such as acetoxymethyl or acetoxypentyl.

The amount of the palladium compound is required to be usually within a range of from 0.005 to 1.0 wt %, preferably from 0.01 to 0.5 wt %, as the palladium concentration in the conversion reaction solution. The amount of the phosphorus compound is usually within a range of from 0.005 to 2.5 wt %, preferably from 0.05 to 2.2 wt %, more preferably from 0.1 to 1.5 wt %, as the phosphorus concentration in the conversion reaction solution. If the palladium and phosphorus concentrations are high, precipitation takes place during the conversion reaction, whereby withdrawal of the solution tends to be difficult. If the palladium concentration is low, the reaction tends to be slow, thus leading to a drawback that it takes a long time for the reaction. If the phosphorus concentration is low, the palladium tends to be metallized and precipitate.

The conversion reaction may be conducted in the presence of a solvent for the reaction. As the solvent for the reaction, any solvent which is capable of dissolving at least partially the diallyl ethers, the palladium compound and the phosphorus compound, may be employed. Examples of the solvent for reaction include ethers such as diethyl ether, dioxane, tetrahydrofuran, ethylene glycol dimethyl ether and tetraethylene glycol dimethyl ether; ketones such as acetone, methyl ethyl ketone, diethyl ketone, methyl isopropyl ketone and ethyl n-butyl ketone; nitriles such as acetonitrile, propionitrile and benzonitrile; aromatic hydrocarbons such as benzene, toluene, xylene and ethylbenzene; alkanes such as pentane, hexane and heptane; alkenes such as hexene or octene; sulfoxides such as dimethylsulfoxide; sulfones such as sulfolane; nitro compounds such as nitrobenzene and nitromethane; pyridine derivatives such as pyridine and α-pyrroline; amines such as triethylamine; amides such as acetamide, propionamide, N,N-dimethylformamide, N,N-dimethylacetamide and N,N-diethylacetamide; alcohols such as methanol, ethanol, n-propanol, isopropanol, n-butanol, isobutanol, t-butanol and n-octanol; and carboxylic acids such as formic acid, acetic acid, propionic acid and butyric acid. These solvents may be used alone or in combination as a solvent mixture.

The present invention has been accomplished on the basis of a discovery that the conversion reactions of diallyl ethers are sequential reactions whereby diallyl ethers are decomposed via allyl alcohols to unsaturated hydrocarbons such as alkadienes and alkatrienes. Namely, the conversion reactions of diallyl ethers can be represented by the following reaction formulas:

$R^1-CH_2-CH=CH-CH_2-O-CH_2-CH=CH-CH_2-R^2 \longrightarrow$ $R^1-CH_2-CH=CH-CH_2OH + CH_2=CH-CH=CH-R^2$ $R^1-CH_2-CH=CH-CH_2OH \longrightarrow$ $CH_2=CH-CH=CH-R^1 + H_2O$ As is evident from the above reaction formulas, the allyl alcohols as the desired products of the present invention are intermediate products in the decomposition process of diallyl ethers to unsaturated hydrocarbons. Accordingly, it is important to set the conditions for the heat treatment for the conversion reaction within proper ranges. Especially, it is necessary to properly set the time for the conversion reaction (heat treatment) depending upon the conversion reaction temperature and the palladium concentration in the conversion reaction solution. Namely, if the reaction time is too long, the reaction products will be unsaturated hydrocarbons such as alkadienes and alkatrienes, and allyl alcohols can not be obtained.

The most remarkable feature of the present invention resides in that by a conversion reaction under certain specific conditions, conversion of diallyl ethers to allyl alcohols has been realized in a surprisingly high yield. In the present invention, as a condition for heat treatment for the conversion reaction, it is important to employ a condition such that the value of function F represented by the following formula is within a range of $0 \leq F < 100$, preferably $0 \leq F < 70$, more preferably $0 < F < 50$, most preferably $0.1 < F < 50$:

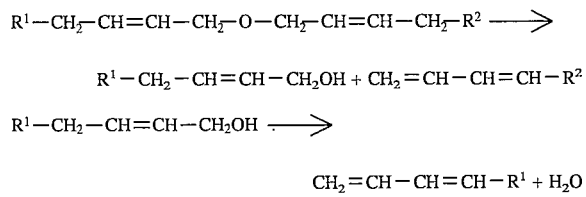

wherein θt is the conversion reaction time (hours), [Pd] is the Pd concentration (wt %) in the conversion reaction solution, and T is the conversion reaction temperature (°C.).

Further, allyl alcohols tend to decompose to unsaturated hydrocarbons. Therefore, it is necessary to control the concentration of allyl alcohols. Namely, the concentration of allyl alcohols in the conversion reaction solution is required to be controlled to a level of not higher 20 wt %, preferably not higher than 18 wt %, more preferably not higher than 15 wt %, most preferably not higher than 10 wt %, not only in the initial stage of the conversion reaction but constantly throughout the reaction.

The temperature for the conversion reaction is usually from 100° to 150° C., preferably from 110° to 140° C., more preferably from 113° to 135° C., most preferably from 118° to 128° C. If the temperature for the conversion reaction is too low, there will be a drawback that the reaction requires a long period of time. On the other hand, if it is too high, there will be drawback that the palladium catalyst is metallized.

The conversion reaction can be carried out under pressure or under reduced pressure and can be satisfactorily conducted by a batch system or a continuous system. It is particularly preferred to conduct the reaction while withdrawing the resulting allyl alcohols formed by conversion reaction, like a reaction distillation. The pressure for the conversion reaction is preferably within a range of from 3 mmHg to 10 kg/cm$^2$, more preferably within a range of from 5 mmHg to atmospheric pressure. If the pressure is too low, the operation will be industrially difficult, and diallyl ethers, etc. will be distilled, whereby the conversion reaction solution will be concentrated too much, whereby the palladium or phosphorus concentration increases to form precipitates, whereby withdrawal of the solution will be difficult.

The conversion reaction time by a batch system and the residence time of the conversion reaction solution in a continuous system, is usually at most 10 hours, preferably from 0.1 to 8 hours, more preferably from 0.3 to 5 hours, most preferably from 0.35 to 3 hours. If the reaction time is too short, the amount of allyl alcohols formed tends to be small, and if it is too long, there will be a drawback that Pd will be metallized. Now, the second aspect of the present invention will be described. In short, this invention is a invention wherein the above described conversion reaction is applied to a hydration dimerization reaction solution containing diallyl ethers as by-products. The hydration dimerization reaction of a conjugated alkadiene with water, i.e. a method for producing allyl alcohols (such as alkadienols) by reacting a conjugated alkadiene and water in the presence of a catalyst containing a palladium compound and a phosphorus compound and, if necessary, carbon dioxide, is disclosed, for example, in Japanese Examined Patent Publication No. 10561/1975 or Japanese Unexamined Patent Publication No. 144306/1979.

The starting material conjugated alkadiene may, for example, be 1,3-butadiene, 2-ethyl-1,3-butadiene, 2,3-dimethl-1,3-butadiene, isoprene, 1,3-pentadiene, chloroprene or 1,3-octadiene. And, as a readily available 1,3-butadiene starting material, so-called BBP (butane-butadiene product), i.e. the C$_4$ fraction mixture in the naphtha decomposition product, may be mentioned in addition to purified 1,3-butadiene.

When BBP is used as the starting material, it is preferred that acetylenes and arenes contained in the BBP starting material are preliminarily decomposed and removed. The total concentration of acetylenes and arenes in the 1,3-butadiene starting material (BBP) is desired to be as low as possible and is usually not higher than about 1.0 wt % relative to 1,3-butadiene. A method for reducing acetylenes and arenes is not particularly limited, and a conventional method may suitably be employed.

The water as another starting material, may be water having a purity to such an extent not to give an influence over the hydration dimerization reaction. The amount of water to be used is not particularly limited, but is selected usually within a range of from 0.5 to 10 mols, preferably from 1 to 5 mols, per mol of the conjugated alkadiene.

As the palladium compound, various conventional palladium compounds which are useful for a hydration dimerization reaction, can be used. Specifically, the palladium compounds mentioned with respect to the above-described conversion reaction, may be employed. The palladium compounds preferred for the above-described conversion reaction are also preferred for the hydration dimerization reaction.

The amount of the palladium compound is suitably determined usually within a range of from 0.00001 to 1 gram atom, preferably from 0.0001 to 0.5 gram atom, as calculated as palladium atoms per mol of the conjugated alkadiene.

As the phosphorus compound, various conventional phosphorus compounds useful for a hydration dimerization reaction can be employed. Specifically, the phosphorus compounds mentioned in the above-described conversion reaction may be employed, and the phosphorus compounds preferred for the above-described conversion reaction are also preferred for the hydration dimerization reaction. Especially, a phosphorus compound having at least 7 carbon atoms in each bond on phosphorus, is preferred from the viewpoint of the selectivity for allyl alcohols (such as alkadienols).

The above phosphorus compound may, for example, be a hydrophobic phosphine such as tritolylphosphine, tris(ethylphenyl)phosphine, trixylylphosphine, trimesitylphosphine, tris(tetramethylphenyl)phosphine or tris(methylmethoxyphenyl)phosphine, or the corresponding phosphite. Among these, tritolylphosphine, trixylylphosphine, trimesitylphosphine or tris(tetramethylphenyl)phosphine is preferred. Such a phosphorus compound has not only an effect to give allyl alcohols (such as alkadienols) at high selectivity in the hydration dimerization reaction, but also an effect to efficiently convert diallyl ethers (such as dialkadienyl ethers) to allyl alcohols in the above-described conversion reaction.

The phosphorus compound is used usually in an amount of from about 0.1 to 100 mols, preferably from about 1 to 50 mols, per gram atom or palladium. However, the amount is not necessarily limited to the above range.

The hydration dimerization reaction is preferably conducted in the presence of a solvent for the reaction in order to smoothly conduct the reaction. As the solvent for the reaction, any solvent which is capable of dissolving the conjugated alkadiene and water at least partially, may be employed. The solvents mentioned in the above-described conversion reaction may all be employed. However, it is advantageous to use a solvent which will have a boiling point lower than water at the time of distillation, since the solvent can readily be separated by distillation in the subsequent step.

The temperature for the hydration dimerization reaction can be selected within a wide range of from room temperature to about 180° C. However, it is preferably within a range of from 50° to 130° C., more preferably from 60° to 100° C. The pressure for the reaction can be selected within a wide range of from atmospheric pressure to about 200 kg/cm$^2$. However, a pressure of from 3 to 70 kg/cm$^2$ is preferred. At the time of the reaction, $CO_2$ may be present in the reaction system, and an inert gas such as helium or argon may also be present, as disclosed in Japanese Examined Patent Publication No. 10565/1975.

The hydration dimerization reaction solution contains, in addition to allyl alcohols as the main products, diallyl ethers and alkatrienes as by-products, an unreacted conjugated alkadiene, the catalyst, water, the solvent, etc. When the conjugated alkadiene is 1,3-butadiene, the main product may be octa-2,7-dien-3-ol, and the by-products may be octa-1,7-dien-3-ol, octatrienes and dioctadienyl ethers. The amounts of these reaction by-products vary depending upon the conditions of the dimerization reaction, but usually around a few mol %, respectively, based on the conjugated alkadiene.

The hydration dimerization reaction solution is usually separated by distillation into allyl alcohols as the main products and a solution (hereinafter referred to as a catalyst solution) containing the catalyst and high boiling point substances such as diallyl ethers as by-products. In the present invention, it is advantageous to apply the above-described conversion reaction when the allyl alcohols are separated by distillation from the reaction solution, and in order to increase the selectivity for allyl alcohols, it is preferred to conduct this conversion reaction at the bottom of the column where the palladium compound, the phosphorus compound and the diallyl ethers are present and to withdraw the formed allyl alcohols from the top of the column. For example, the solvent is distilled off from the hydration dimerization reaction solution, the bottoms are subjected to oil-water separation to obtain a reaction product solution containing the catalyst, allyl alcohols and diallyl ethers, and then the allyl alcohols are separated by distillation from the reaction product solution, while the conversion reaction is carried out at the bottom of the distillation column; or the conversion reaction is carried out at the bottom of the distillation column while allyl alcohols are separated by distillation from a reaction solution obtained after separating at least a part of the allyl alcohols from the hydration dimerization reaction solution; or the conversion reaction may be applied to diallyl ethers as by-products after they have been separated from the catalyst component by a combination of operations such as distillation and extraction.

When the above-described conversion reaction is applied to the catalyst solution, the catalyst solution already contains the palladium compound and the phosphorus compound (such as a phosphine or a phosphite). This is advantageous in that it is unnecessary to separately add such compounds for the conversion reaction. In a case where the above-described conversion reaction is applied to diallyl ethers after they have been separated from the catalyst component, the conversion reaction may be carried out by adding the palladium compound as a catalyst. Further, if necessary, the catalyst solution may be mixed again to the diallyl ethers separated from the catalyst solution.

In any case, it is necessary to adopt, as a condition for heat treatment for the conversion reaction, such a condition that the value of function F represented by the above-mentioned formula is within a range of $0 \leq F < 100$, preferably $0 \leq F < 70$, more preferably $0 < F < 50$, most preferably $0.1 < F < 50$. Further, the concentration of allyl alcohols in the conversion reaction solution is required to be controlled to a level of not higher than 20 wt %, preferably not higher than 18 wt %, more preferably not higher than 15 wt %, most preferably not higher than 10 wt %.

Now, the present invention will be described in further detail with reference to Examples. However, it should be understood that the present invention is by no means restricted to such specific Examples.

EXAMPLE 1

Into a 200 ml stainless steel autoclave equipped with an electromagnetic induction stirrer, 60 g of bis(2,7-octadienyl)ether, 5 g of hydroxyoctadiene, 1.0 g of bis(tri-o-tolylphosphine)palladium (0) and 7 g of tri-o-tolylphosphine were charged. The Pd concentration was 0.2 wt %. Then, in a $N_2$ atmosphere, the conversion reaction was carried out at 140° C. for one hour. The value of function F under this condition was 8. The obtained reaction solution was analyzed by gas chromatography to obtain the reacted amount of bis(2,7-octadienyl)ether and the amount of hydroxyoctadiene formed. The results are shown in Table 1 together with the reaction conditions.

EXAMPLE 2

The conversion reaction was carried out in the same manner as in Example 1 except that in Example 1, the reaction temperature was changed to 120° C., the reaction time was changed to 3 hours and the value of function F was changed to 12, and then the reaction solution was analyzed. The results are shown in Table 1 together with the reaction conditions.

EXAMPLE 3

Into the same autoclave as used in Example 1, 60 g of bis(2,7-octadienyl)ether, 5 g of hydroxyoctadiene, 1.5 g of bis(tri-2,5-xylylphosphine)palladium (0), and 7 g of tri-2,5-xylylphosphine were charged. The Pd concentration was 0.3 wt %. Then, in a $N_2$ atmosphere, the conversion reaction was carried out at 130° C. for 3 hours. The value of function F under this condition was 27. The obtained reaction solution was analyzed by gas chromatography to obtain the reacted amount of bis(2,7-octadienyl)ether and the amount of hydroxyoctadiene formed. The results are shown in Table 1 together with the reaction conditions.

EXAMPLE 4

Into the same autoclave as used in Example 1, 60 g of bis(2,7-octadienyl)ether, 2 g of hydroxyoctadiene, 0.7 g of palladium (II) acetyl acetonate, and 7 g of trioctylphosphine were charged. The Pd concentration was 0.3 wt %. Then, in a $N_2$ atmosphere, the conversion reaction was carried out at 130° C. for 2 hours. The value of function F under this condition was 18. The obtained reaction solution was analyzed by gas chromatography to obtain the reacted amount of bis(2,7-octadienyl)ether and the amount of hydroxyoctadiene formed. The results are shown in Table 1 together with the reaction conditions.

EXAMPLE 5

Into the same autoclave as used in Example 1, 60 g of bis(2,7-octadienyl)ether, 0.6 g of tri(2,5-xylyl)phosphine and 0.013 g of palladium acetate were charged. The Pd concentration was 0.01 wt %. Then, in a $N_2$ atmosphere, the conversion reaction was carried out at 120° C. for 3 hours. The value of function F under this condition was 0.6. The obtained reaction solution was analyzed by gas chromatography to obtain the reacted amount of bis(2,7-octadienyl)ether and the amount of hydroxyoctadiene formed. The concentration of hydroxyoctadiene after the reaction was 1.4 wt %. The results are shown in Table 1 together with the reaction conditions.

TABLE 1

|  | Temp. (°C.) | Time (hr) | Pd concentration (wt %) | Value F | Reacted amount (g) | Formed amount (g) | Selectivity (%) | HOD concentration in the feed (wt %) | HOD concentration after the conversion reaction (wt %) |
| --- | --- | --- | --- | --- | --- | --- | --- | --- | --- |
| Example 1 | 140 | 1 | 0.2 | 8 | 19.6 | 2.6 | 24.6 | 6.8 | 10.4 |
| Example 2 | 120 | 3 | 0.2 | 12 | 7.1 | 1.2 | 31.3 | 6.8 | 8.5 |
| Example 3 | 130 | 3 | 0.3 | 27 | 21.5 | 3.0 | 25.9 | 6.8 | 10.9 |
| Example 4 | 130 | 2 | 0.3 | 18 | 8.0 | 1.0 | 23.2 | 2.9 | 4.3 |
| Example 5 | 120 | 3 | 0.01 | 0.6 | 1.8 | 0.85 | 87.7 | 0.0 | 1.4 |

In the above Table, HOD represents hydroxyoctadiene, and the selectivity is represented by the ratio of the mols of the formed product to the mols of the reactant (molecular weight of bis(2,7-octadienyl)ether: 234.4, molecular weight of hydroxyoctadiene: 126.2).

COMPARATIVE EXAMPLE 1

The conversion reaction was carried out in the same manner as in Example 1 except that in Example 1, the reaction temperature was changed to 90° C., the reaction time was changed to 0.2 hour, and the value of function F was changed to −0.4, and then the reaction solution was analyzed to obtain the conversion of bis(2,7-octadienyl)ether and the amount of hydroxyoctadiene formed. As a result, the reacted amount of bis(2,7-octadienyl)ether was 0.2 g, but the concentration of hydroxyoctadiene did not increase, thus indicating no formation.

COMPARATIVE EXAMPLE 2

Into the same stainless steel autoclave as used in Example 1, 60 g of bis(2,7-octadienyl)ether, 5 g of hydroxyoctadiene, 1.4 g of bis(tri-o-tolylphosphine)palladium (0), and 7 g of tri-otolylphosphine were charged. The Pd concentration was 0.3 wt %, and the concentration of hydroxyoctadiene was 6.8 wt %. Then, in a $N_2$ atmosphere, the conversion reaction was carried out at 140° C. for 10 hours. The value of function F under this condition was 120. The obtained reaction solution was analyzed by gas chromatography to obtain the reacted amount of bis(2,7-octadienyl)ether and the amount of hydroxyoctadiene formed. As a result, the reacted amount of bis(2,7-octadienyl)ether was 58.0 g, but no hydroxyoctadiene was detected. Further, metallization of the Pd catalyst was observed.

COMPARATIVE EXAMPLE 3

A mixture comprising 0.5 mol of 1,3-butadiene, 1 mol of water, 0.6 mol of carbon dioxide, 0.5 mmol of bis(acetylacetone)palladium, 2.0 mmol of triphenylphosphine and 63 ml of dimethylformamide, was charged into a stainless steel autoclave having an internal capacity of 0.3 l and equipped with an electromagnetic induction stirrer, and a hydration dimerization reaction was carried out at 90° C. for 3 hours.

To the obtained reaction solution, 1.0 mmol of triphenylphosphine was added, followed by distillation at a bath temperature of 90° C. under a pressure of 1.8 mmHg to distill off octadienyl alcohol. The Pd concentration in the bottom was 1.41 wt %, the P concentration was 2.45 wt %, the concentration of hydroxyoctadiene was 3 wt %, and the concentration of bis(2,7-octadienyl)ether was 14 wt %. Then, distillation operation under heating was carried out for 15 minutes at a bath temperature of 120° C. under a pressure of 1.8 mmHg, whereby precipitates were formed in the bottom. The Pd concentration in the bottom inclusive of the precipitates was 2.2 wt %, and the P concentration was 2.56 wt %.

COMPARATIVE EXAMPLE 4

Into the same autoclave as used in Example 1, 60 g of bis(2,7-octadienyl)ether, 30 g of hydroxyoctadiene, 1.5 g of bis(tri-2,5-xylylphosphine)palladium (0) and 7 g of tri-2,5-xylylphosphine were charged. The Pd concentration was 0.2 wt %, and the concentration of hydroxyoctadiene was 30 wt %. Then, in a $N_2$ atmosphere, the conversion reaction was carried out at 130° C. for 2 hours. The value of function F under this condition was 12. The obtained reaction solution was analyzed by gas chromatography to obtain the reacted amount of bis(2,7-octadienyl)ether and the amount of hydroxyoctadiene formed. As a result, the reacted amount of bis(2,7-octadienyl)ether was 17.6 g, but the amount of hydroxyoctadiene did not increase by decrease as much as 19 g.

COMPARATIVE EXAMPLE 5

Into the same autoclave as used in Example 1, 60 g of bis(2,7-octadienyl)ether, 0.03 g of tri(2,5-xylyl)phosphine and 0.013 g of palladium acetate were charged. The Pd concentration was 0.01 wt %. Then, in a $N_2$ atmosphere, the conversion reaction was carried out at 120° C. for 8 hours. The value of function F under this condition was 1.6. The reaction solution was analyzed, whereby no substantial reaction of bis(2,7-octadienyl)ether was observed although formation of a trace amount of hydroxyoctadiene was observed. Further, due to metallization of Pd, the reaction solution was turbid with a black color.

EXAMPLE 6

A hydration dimerization reaction of 1,3-butadiene and water was carried out as follows. Namely, into a 10 l stainless steel autoclave equipped with an electromagnetic induction stirrer, 1000 g of 1,3-butadiene, 320 g of water, 1.4 g of bis(acetylacetone)palladium, 17.2 g of tri(o-tolyl)phosphine and 2587 g of acetone were charged and pressurized to 20 $kg/cm^2G$ with carbon dioxide, and the hydration dimerization reaction was carried out at 90° C. for 3 hours.

The obtained reaction solution was distilled under atmospheric pressure to separate a low boiling point component composed mainly of acetone. The distillation residual liquid was left to stand still, after separating and removing the aqueous phase, hydroxyoctadiene was separated by a thin film evaporator. The thin film evaporation was operated under a pressure of 20 mmHg and at a heater temperature of 140° C.

60 g of the obtained evaporation residual liquid composed mainly of dioctadienyl ether was charged into a 200 ml stainless steel autoclave equipped with an electromagnetic induction stirrer, and the conversion reaction was carried out at 120° C. for 1 hour. The HOD concentration in the distillation residual liquid charged into the autoclave was 3.5 wt %, and the HOD concentration after the conversion reaction was 7.0 wt %. The Pd concentration in the distillation residual liquid was measured by a high frequency emission spectral analyzer, whereby it was found to be 0.15 wt %. The value of function F in the above conversion reaction was 3. The evaporation residual liquid and the reaction solution were analyzed by gas chromatography, and the results are shown in Table 2. From the results of the analyses, the reacted amount of dioctadienyl ether was 9.4 g, the formed amount of hydroxyoctadiene was 2.1 g, and the selectivity was 41.5%.

TABLE 2

| Components | Composition of the distillation residual liquid (wt %) | Weight before the reaction (g) | Weight after the reaction (g) |
| --- | --- | --- | --- |
| Hydroxyoctadiene | 3.5 | 2.1 | 4.2 |
| Dioctadienyl ether | 56 | 33.6 | 24.2 |
| Tri-o-tolylphosphine | 5 | — | — |

EXAMPLE 7

The operations from the hydration dimerization reaction to the thin film evaporation were carried out in the same manner as in Example 6 except that in Example 6, tri(2,5-xylyl)phosphine was used instead of tri(o-tolyl)phosphine, and the heater for the thin film evaporation was adjusted to 120° C. Then, the obtained evaporation residual liquid composed mainly of dioctadienyl ether, was supplied to a simple distillation apparatus made of glass, and continuous distillation was carried out. The supply rate was 86 g/hr, the vessel temperature was 120° C., the distillation pressure was 20 mmHg, and the residence time (reaction time) in the vessel was 1.8 hours. The concentration of hydroxyoctadiene in the supplied evaporation residual liquid was 19.8 wt %. The amount of the liquid in the vessel was controlled to be 70 ml, whereby the average amount of bottoms was 38 g/hr, and the average amount of distillate was 48 g/hr. The concentration of hydroxyoctadiene in the bottoms was 7.3 wt %, and the Pd concentration in the bottoms was measured by a high frequency emission spectral analyzer, whereby it was found to be 0.2 wt %. In the above distillation operation, the value of function F in the heat treatment (conversion reaction) in the vessel was 7.2. The supplied liquid was analyzed by gas chromatography, whereby the supplied amounts of dioctadienyl ether and hydroxyoctadiene were found to be 49.0 g/hr and 17.0 g/hr, respectively. Further, similar analysis was carried out with respect to a mixed solution of the distillate and the bottoms, whereby the total amounts of dioctadienyl ether and hydroxyoctadiene were 37.7 g/hr and 19.7 g/hr, respectively. From these results, the reacted amount of dioctadienyl ether was found to be 11.34 g/hr, and the formed amount of hydroxyoctadiene was found to be 2.7 g/hr, and the selectivity was found to be 44%.

EXAMPLE 8

Using the apparatus as shown in FIG. 1, the reaction of 1,3-butadiene and water was continuously operated while recycling the catalyst solution. As a reactor 1, a stainless steel autoclave having an internal capacity of 10l, and equipped with an induction stirrer, was used, and a recycling catalyst solution containing high boiling point by-products and acetone as a recycling solvent, water and 1,3-butadiene were continuously supplied. At that time, the interior of the autoclave was maintained at 10 kg/cm2G by carbon dioxide, the reaction temperature was 75° C., the amount of the liquid in the reactor was 5l, and the residence time of the reaction solution was 5.1 hours. The reaction was carried out by means of palladium acetate and tri(2,5-xylyl)phosphine. The reaction solution continuously withdrawn from the reactor was supplied to a gas-liquid separator 2, and the liquid separated at 30° C. under 1 kg/cm$^2$G, was continuously supplied to a distillation column 3. The distillation column 3 was operated with a theoretical plate number of 15 plates under the column top pressure of 760 mmHg and a reflux ratio of 1. The acetone solvent distilled from the top of the distillation column 3 was returned to the reactor, while the bottoms were subjected to oil-water separation by an oil-water separator 4, whereupon the oil phase was withdrawn as the reaction product solution. The oil phase containing octadienol and dioctadienyl ether as a by-product, was continuously supplied to a distillation column 5 and subjected to a conversion reaction to allyl alcohol. The distillation column 5 was operated with a theoretical plate number of 5 plates under a column top pressure of 20 mmHg and a column bottom temperature of 120° C., and the amount of the liquid at the bottom of the column was adjusted so that the amount of the bottoms would be about 100 g/hr. The residence time at the bottom of the distillation column was 0.75 hr, and the value for function F was 1.5.

Further, the bottoms from the distillation column 5 were recycled as a catalyst solution to the reactor. The analytical values relating to the distillation column 5 upon expiration of 800 hours were as shown in Table 3. Namely, 13% of dioctadienyl ether was decomposed, the recovery rate of 1-hydroxyoctadiene was 101%, the recovery rate of 3-hydroxyoctadiene was 109%, and the selectivity of dioctadienyl ether to hydroxyoctadiene was 49%.

TABLE 3

| | Reaction product solution | | Bottoms | | Distillate | |
| --- | --- | --- | --- | --- | --- | --- |
| | Concentration (wt %) | Flow rate (g/hr) | Concentration (wt %) | Amount | Concentration (wt %) | Flow rate (g/hr) |
| 1-Hydroxyoctadiene | 53.72 | 200.3 | 14.77 | 16.68 | 71.48 | 186.8 |
| 3-Hydroxyoctadiene | 2.28 | 8.58 | 0.33 | 0.37 | 3.45 | 8.97 |
| Dioctadienyl ether | 23.12 | 86.22 | 51.78 | 58.52 | 6.41 | 16.66 |
| Palladium | | | 0.10 | | | |
| Phosphorus | | | 0.55 | | | |
| Total | | 383 | | 113 | | 260 |

As described in the foregoing, according to the present invention, it is possible to produce allyl alcohols from corresponding diallyl ethers. Especially, in a method for producing allyl alcohols by a hydration dimerization reaction of a conjugated alkadiene, it is possible to convert diallyl ethers as by-products to allyl alcohols to increase the yield of allyl alcohols, and yet, unnecessary high boiling point products can be converted to low boiling point components which are readily separable, whereby it is possible to avoid a loss of an expensive catalyst.

What is claimed is:

1. A method for producing allyl alcohols, which comprises heat-treating diallyl ethers in the presence of a catalyst containing a palladium compound and a phosphorus compound to convert them to allyl alcohols, wherein the heat treatment is conducted under such conversion reaction conditions that the value of function F represented by the following formula is within a range of $0 \leq F < 100$, the concentration of allyl alcohols in the conversion reaction solution is not higher than 20 wt %, and the Pd concentration in the conversion reaction solution is within a range of from 0.005 to 1.0 wt %:

$$F = \theta t \cdot [Pd] \cdot (T - 100)$$

wherein $\theta t$ is the conversion reaction time (hours), [Pd] is the Pd concentration (wt %) in the conversion reaction solution, and T is the conversion reaction temperature (°C.).

2. The method for producing allyl alcohols according to claim 1, wherein the value of function F is within a range of $0 \leq F < 70$.

3. The method for producing allyl alcohols according to claim 1, wherein the phosphorus concentration in the conversion reaction solution is within a range of from 0.005 to 2.5 wt %.

4. The method for producing allyl alcohols according to claim 1, wherein the phosphorus compound is a hydrophobic phosphine compound.

5. The method for producing allyl alcohols according to claim 4, wherein the phosphorus compound is selected from the group consisting of triphenylphosphine, tritolylphosphine, trixylylphosphine, trimesitylphosphine and tris(tetramethylphenyl)phosphine.

6. The method for producing allyl alcohols according to claim 1, wherein the heat treatment is conducted under such conditions that the conversion reaction temperature T is within a range of from 100° to 150° C., and the conversion reaction time $\theta t$ is within a range of from 0.1 to 8 hours.

7. The method for producing allyl alcohols according to claim 1, wherein diallyl ethers are dialkadienyl ethers, and the allyl alcohols are alkadienols.

8. A method for producing allyl alcohols, which comprises subjecting a conjugated alkadiene and water to a hydration dimerization reaction in the presence of a catalyst containing a palladium compound and a phosphorus compound and, if necessary, carbon dioxide to obtain a hydration dimerization reaction solution containing allyl alcohols and diallyl ethers as by-products, and then heat-treating the diallyl ethers in the reaction solution for conversion to allyl alcohols, wherein the heat treatment is conducted under such conversion reaction conditions that the value of function F represented by the following formula is within a range of $0 \leq F < 100$, the concentration of the allyl alcohols in the conversion reaction solution is not higher than 20 wt %, and the Pd concentration in the conversion reaction solution is within a range of from 0.005 to 1.0 wt %:

$$F = \theta t \cdot [Pd] \cdot (T - 100)$$

wherein $\theta t$ is the conversion reaction time (hours), [Pd] is the Pd concentration (wt %) in the conversion reaction solution, and T is the conversion reaction temperature (°C.).

9. The method for producing allyl alcohols according to claim 8, wherein the value of function F is within a range of $0 \leq F < 70$.

10. The method for producing allyl alcohols according to claim 8, wherein the phosphorus concentration in the conversion reaction solution is within a range of from 0.005 to 2.5 wt %.

11. The method for producing allyl alcohols according to claim 8, wherein the phosphorus compound is a hydrophobic phosphine compound.

12. The method for producing allyl alcohols according to claim 11, wherein the phosphorus compound is selected from the group consisting of tritolylphosphine, trixylylphosphine, trimesitylphosphine and tris(tetramethylphenyl)phosphine.

13. The method for producing allyl alcohols according to claim 8, wherein the heat treatment is conducted under such conditions that the conversion reaction temperature T is within a range of from 100° to 150° C., and the conversion reaction time $\theta t$ is within a range of from 0.1 to 8 hours.

14. The method for producing allyl alcohols according to claim 8, wherein the conjugated alkadiene is 1,3-butadiene.

15. The method for producing allyl alcohols according to claim 8, wherein the diallyl ethers are dialkadienyl ethers, and the allyl alcohols are alkadienols.

16. A method for producing allyl alcohols, which comprises subjecting a conjugated alkadiene and water to hydration dimerization reaction in a solvent in the presence of a catalyst containing a palladium compound and a phosphorus compound and, if necessary, carbon dioxide to obtain a hydration dimerization reaction solution containing allyl alcohols and diallyl ethers as by-products, and then heat-treating the diallyl ethers in the reaction solution for conversion to allyl alcohols, wherein the heat treatment is conducted when the allyl alcohols are separated by distillation from the reaction solution under such conversion reaction conditions that the value of function F represented by the following formula is within a range of $0 \leq F < 100$, the concentration of allyl alcohols in the conversion reaction solution is not higher than 20 wt %, and the Pd concentration in the conversion reaction solution is within a range of from 0.005 to 1.0 wt %:

$$F = \theta t \cdot [Pd] \cdot (T - 100)$$

wherein $\theta t$ is the conversion reaction time (hours), [Pd] is the Pd concentration (wt %) in the conversion reaction solution, and T is the conversion reaction temperature (°C.).

17. The method for producing allyl alcohols according to claim 16, wherein the solvent is distilled off from the hydration dimerization reaction solution by distillation, the bottoms are subjected to oil-water separation to obtain a reaction product solution containing the catalyst, the allyl alcohols and the diallyl ethers, and then the allyl alcohols are separated by distillation from the reaction product solution, wherein the conversion reaction is carried out at the bottom of the distillation column.

18. The method for producing allyl alcohols according to claim 16, wherein the solvent for the hydration dimerization reaction is a solvent which is made to have a lower boiling point than water at the time of distillation.

19. The method for producing allyl alcohols according to claim 16, wherein the conversion reaction is carried out at the bottom of the distillation column while allyl alcohols are separated by distillation from a reaction solution obtained after separating at least a part of the allyl alcohols from the hydration dimerization reaction solution.

* * * * *